United States Patent
Gray

(10) Patent No.: US 8,041,433 B2
(45) Date of Patent: Oct. 18, 2011

(54) MAGNETIC RESONANCE IMAGING INTERFERENCE IMMUNE DEVICE

(75) Inventor: Robert W. Gray, Rochester, NY (US)

(73) Assignee: Medtronic, Inc., Minneapolis, MN (US)

( * ) Notice: Subject to any disclaimer, the term of this patent is extended or adjusted under 35 U.S.C. 154(b) by 498 days.

(21) Appl. No.: 11/208,065

(22) Filed: Aug. 19, 2005

(65) Prior Publication Data

US 2006/0041294 A1     Feb. 23, 2006

Related U.S. Application Data

(60) Provisional application No. 60/603,476, filed on Aug. 20, 2004.

(51) Int. Cl.
*A61N 1/05* (2006.01)
(52) U.S. Cl. ......... 607/116; 607/119; 607/121; 607/122
(58) Field of Classification Search ................ 607/119, 607/122, 121, 116
See application file for complete search history.

(56) References Cited

U.S. PATENT DOCUMENTS

| | | | |
|---|---|---|---|
| 5,217,010 A | 6/1993 | Tsitlik et al. | |
| 5,727,552 A | 3/1998 | Ryan | |
| 5,964,705 A | 10/1999 | Truwit et al. | |
| 6,032,063 A | 2/2000 | Hoar et al. | |
| 6,280,385 B1 | 8/2001 | Melzer et al. | |
| 6,393,314 B1 | 5/2002 | Watkins et al. | |
| 6,471,645 B1 | 10/2002 | Warkentin et al. | |
| 6,496,006 B1 | 12/2002 | Vrijheid | |
| 6,501,978 B2 | 12/2002 | Wagshul et al. | |
| 6,503,272 B2 | 1/2003 | Duerig et al. | |
| 6,506,972 B1 | 1/2003 | Wang | |
| 6,564,084 B2 | 5/2003 | Allred, III et al. | |
| 6,673,999 B1 | 1/2004 | Wang et al. | |
| 6,700,472 B2 | 3/2004 | Wang et al. | |
| 6,701,176 B1 | 3/2004 | Halperin et al. | |
| 6,713,671 B1 | 3/2004 | Wang et al. | |
| 6,765,144 B1 | 7/2004 | Wang et al. | |
| 6,815,609 B1 | 11/2004 | Wang et al. | |
| 6,822,548 B2 | 11/2004 | Wang et al. | |
| 6,824,512 B2 | 11/2004 | Warkentin et al. | |
| 6,844,492 B1 | 1/2005 | Wang et al. | |
| 6,846,985 B2 | 1/2005 | Wang et al. | |
| 6,847,837 B1 | 1/2005 | Melzer et al. | |
| 6,864,418 B2 | 3/2005 | Wang et al. | |
| 6,876,886 B1 | 4/2005 | Wang | |
| 6,906,256 B1 | 6/2005 | Wang | |
| 7,013,180 B2 | 3/2006 | Villaseca et al. | |
| 2002/0111542 A1 | 8/2002 | Warkentin et al. | |
| 2002/0138135 A1 | 9/2002 | Duerig et al. | |
| 2003/0018369 A1 | 1/2003 | Thompson et al. | |
| 2003/0036776 A1 | 2/2003 | Foster et al. | |
| 2003/0050557 A1 | 3/2003 | Susil et al. | |

(Continued)

FOREIGN PATENT DOCUMENTS

FR     2494118 A1     5/1982

*Primary Examiner* — Niketa I Patel
*Assistant Examiner* — Rex Holmes
(74) *Attorney, Agent, or Firm* — Stephen W. Bauer; Michael J. Ostrom

(57) ABSTRACT

A wire form includes a conductor having a distal end and a proximal end. The conductor is coiled and has a predetermined spacing between adjacent coils. The predetermined spacing provides a parasitic capacitance and an inductance. The parasitic capacitance and inductance have a resonance frequency tuned to about an excitation signal's frequency of a magnetic-resonance imaging scanner.

14 Claims, 3 Drawing Sheets

U.S. PATENT DOCUMENTS

| | | |
|---|---|---|
| 2003/0083723 A1 | 5/2003 | Wilkinson et al. |
| 2003/0083726 A1 | 5/2003 | Zeijlemaker et al. |
| 2003/0120148 A1 | 6/2003 | Pacetti |
| 2003/0135114 A1 | 7/2003 | Pacetti et al. |
| 2003/0171670 A1 | 9/2003 | Gumb et al. |
| 2004/0077995 A1 | 4/2004 | Ferek-Petric et al. |
| 2004/0078067 A1 | 4/2004 | Thompson et al. |
| 2004/0164836 A1 | 8/2004 | Wang et al. |
| 2004/0176822 A1 | 9/2004 | Thompson et al. |
| 2004/0210289 A1 | 10/2004 | Wang et al. |
| 2004/0249428 A1 | 12/2004 | Wang et al. |
| 2004/0249440 A1 | 12/2004 | Bucker et al. |
| 2004/0263172 A1 | 12/2004 | Gray et al. |
| 2004/0263173 A1 | 12/2004 | Gray et al. |
| 2004/0263174 A1 | 12/2004 | Gray et al. |
| 2005/0043761 A1 | 2/2005 | Connelly et al. |
| 2005/0155779 A1 | 7/2005 | Wang et al. |
| 2005/0197677 A1 | 9/2005 | Stevenson |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0229693 A1 | 10/2006 | Bauer et al. |
| 2006/0247684 A1 | 11/2006 | Halperin et al. |
| 2006/0247747 A1 | 11/2006 | Olsen et al. |
| 2006/0247748 A1 | 11/2006 | Wahlstrand et al. |

MAGNETIC RESONANCE IMAGING INTERFERENCE IMMUNE DEVICE

PRIORITY INFORMATION

The present application claims priority, under 35 U.S.C.§119(e), from U.S. Provisional Patent Application Ser. No. 60/603,476, filed on Aug. 20, 2004. The entire content of U.S. Provisional Patent Application Ser. No. 60/603,476, filed on Aug. 20, 2004, is hereby incorporated by reference.

FIELD OF THE PRESENT INVENTION

The present invention is directed to a device for protecting a patient, physician, and/or electronic components in an electrical device implanted or partially implanted within the patient. More particularly, the present invention is directed to a device for protecting the conductive parts of the electrical device from current and voltage surges induced by magnetic resonance imaging systems' oscillating magnetic fields.

BACKGROUND OF THE PRESENT INVENTION

Magnetic resonance imaging has been developed as an imaging technique adapted to obtain both images of anatomical features of human patients as well as some aspects of the functional activities and characteristics of biological tissue. These images have medical diagnostic value in determining the state of the health of the tissue examined. Unlike the situation with fluoroscopic imaging, a patient undergoing magnetic resonance imaging procedure may remain in the active imaging system for a significant amount of time, e.g. a half-hour or more, without suffering any adverse effects.

In a magnetic resonance imaging process, a patient is typically aligned to place the portion of the patient's anatomy to be examined in the imaging volume of the magnetic resonance imaging apparatus. Such a magnetic resonance imaging apparatus typically comprises a primary electromagnet for supplying a constant magnetic field ($B_0$) which, by convention, is along the z-axis and is substantially homogeneous over the imaging volume and secondary electromagnets that can provide linear magnetic field gradients along each of three principal Cartesian axes in space (generally x, y, and z, or $x_1$, $x_2$ and $x_3$, respectively). The magnetic resonance imaging apparatus also comprises one or more radio frequency coils that provide excitation and detection of the magnetic resonance imaging induced signals in the patient's body.

The gradient fields are switched ON and OFF at different rates depending on the magnetic resonance imaging scan sequence used. In some cases, this may result in a changing magnetic field on the order of dB/dt=50 T/s. The frequency that a gradient field may be turned ON can be between 200 Hz to about 300 kHz.

For a single loop with a fixed area, Lenz's law can be stated as:

$$EMF = -A \cdot dB/dt$$

where A is the area vector, B is the magnetic field vector, and "·" is the vector scalar product. This equation indicates that an electro-motive-force (EMF) is developed in any loop that encircles a changing magnetic field.

In a magnetic resonance imaging system, there is applied to the biological sample (patient) a switched gradient field in all 3 coordinate directions (x-, y-, z- directions). If the patient has an implanted heart pacemaker (or other implanted devices having conductive components) the switched gradient magnetic fields (an alternating magnetic field) may cause erroneous signals to be induced/generated in a sensing lead or device or circuit; damage to electronics; and/or harmful stimulation of tissue, e.g. heart muscle, nerves, etc.

As noted above, the use of the magnetic resonance imaging process with patients who have implanted medical assist devices; such as cardiac assist devices or implanted insulin pumps; often presents problems. As is known to those skilled in the art, implantable devices (such as implantable pulse generators and cardioverter/defibrillator/pacemakers) are sensitive to a variety of forms of electromagnetic interference because these enumerated devices include sensing and logic systems that respond to low-level electrical signals emanating from the monitored tissue region of the patient. Since the sensing systems and conductive elements of these implantable devices are responsive to changes in local electromagnetic fields, the implanted devices are vulnerable to external sources of severe electromagnetic noise, and in particular, to electromagnetic fields emitted during the magnetic resonance imaging procedure. Thus, patients with implantable devices are generally advised not to undergo magnetic resonance imaging procedures.

To more appreciate the problem, the use of implantable cardiac assist devices during a magnetic resonance imaging process will be briefly discussed.

The human heart may suffer from two classes of rhythmic disorders or arrhythmias: bradycardia and tachyarrhythmia. Bradycardia occurs when the heart beats too slowly, and may be treated by a common implantable pacemaker delivering low voltage (about 3 V) pacing pulses.

The common implantable pacemaker is usually contained within a hermetically sealed enclosure, in order to protect the operational components of the device from the harsh environment of the body, as well as to protect the body from the device.

The common implantable pacemaker operates in conjunction with one or more electrically conductive leads, adapted to conduct electrical stimulating pulses to sites within the patient's heart, and to communicate sensed signals from those sites back to the implanted device.

Furthermore, the common implantable pacemaker typically has a metal case and a connector block mounted to the metal case that includes receptacles for leads which may be used for electrical stimulation or which may be used for sensing of physiological signals. The battery and the circuitry associated with the common implantable pacemaker are hermetically sealed within the case. Electrical interfaces are employed to connect the leads outside the metal case with the medical device circuitry and the battery inside the metal case.

Electrical interfaces serve the purpose of providing an electrical circuit path extending from the interior of a hermetically sealed metal case to an external point outside the case while maintaining the hermetic seal of the case. A conductive path is provided through the interface by a conductive pin that is electrically insulated from the case itself.

Such interfaces typically include a ferrule that permits attachment of the interface to the case, the conductive pin, and a hermetic glass or ceramic seal that supports the pin within the ferrule and isolates the pin from the metal case.

A common implantable pacemaker can, under some circumstances, be susceptible to electrical interference such that the desired functionality of the pacemaker is impaired. For example, common implantable pacemaker requires protection against electrical interference from electromagnetic interference (EMI), defibrillation pulses, electrostatic discharge, or other generally large voltages or currents generated by other devices external to the medical device. As noted above, more recently, it has become crucial that cardiac assist systems be protected from magnetic-resonance imaging sources.

Such electrical interference can damage the circuitry of the cardiac assist systems or cause interference in the proper operation or functionality of the cardiac assist systems. For example, damage may occur due to high voltages or excessive currents introduced into the cardiac assist system.

Moreover, problems are realized when the placement of the implant is next to particular organs. For example, when a pacemaker is placed in the upper chest and the lead tip is placed into the heart, a loop (an electrical loop) is created. A changing magnetic field (the switched gradient field) over the area of the loop (through the area of the loop) will cause an induced voltage (and current) across the heart. This induced voltage (current) can stimulate the heart inappropriately and can cause heart damage or death.

It is further noted that uncoated wire forms used by in-vivo devices, such as pacing leads, do not have significantly less DC resistance than coated wire forms because it appears that the current path is the same for the uncoated and coated wires. In other words, an apparent oxidation layer on the uncoated wire results in essentially a resistive coating over the "uncoated" wire form. Thus, the current does not flow through adjacent coil loop contact points but instead follows the curvature of the wire, just as in the case of the coated wire.

At a magnetic resonance imaging scanner's frequency, approximately 63.85 MHz, both uncoated and coated wire forms have the characteristics of capacitors, not inductors. It is apparent that parasitic capacitance is formed between adjacent loops in the wire and is the dominate characteristic of the wire at approximately 63.85 MHz. This parasitic capacitance enables electrical current to flow into and out of the wire form due to several mechanisms, including the oscillating electrical field set up in the body by the magnetic resonance imaging unit. In a pacing lead, this condition creates a high current density at the exposed electrode located at the distal end of the lead.

Therefore, it is desirable to provide wire forms which shift the resonance frequency of the wire form towards approximately 63.85 MHz, the resonance frequency of a magnetic resonance imaging scanner, thereby changing the wire form's characteristics to that of an inductor, which has the property of adding impedance to the flow of AC current induced by the magnetic resonance imaging unit.

SUMMARY OF THE PRESENT INVENTION

One aspect of the present invention is a wire form. The wire form includes a conductor having a distal end and a proximal end. The conductor is coiled and has a predetermined spacing between adjacent coils. The predetermined spacing provides a parasitic capacitance and an inductance. The parasitic capacitance and inductance have a resonance frequency shifted towards an excitation signal's frequency of a magnetic-resonance imaging scanner.

Another aspect of the present invention is a method for forming a wire form by stretching a spring wire form to create gaps between adjacent coils, the gaps providing a parasitic capacitance and an inductance, the parasitic capacitance and inductance having a resonance frequency shifted towards an excitation signal's frequency of a magnetic-resonance imaging scanner.

Another aspect of the present invention is a method for forming a wire form by coating a conductor with an electrically insulative layer, an electrically conductive shielding layer, and a protective and electrically insulative layer; and coiling the coated conductor such that the coiled coated conductor provides a parasitic capacitance and an inductance, the parasitic capacitance and inductance having a resonance frequency shifted towards an excitation signal's frequency of a magnetic-resonance imaging scanner.

BRIEF DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein.

DESCRIPTION OF THE PRESENT INVENTION

Figure 1:
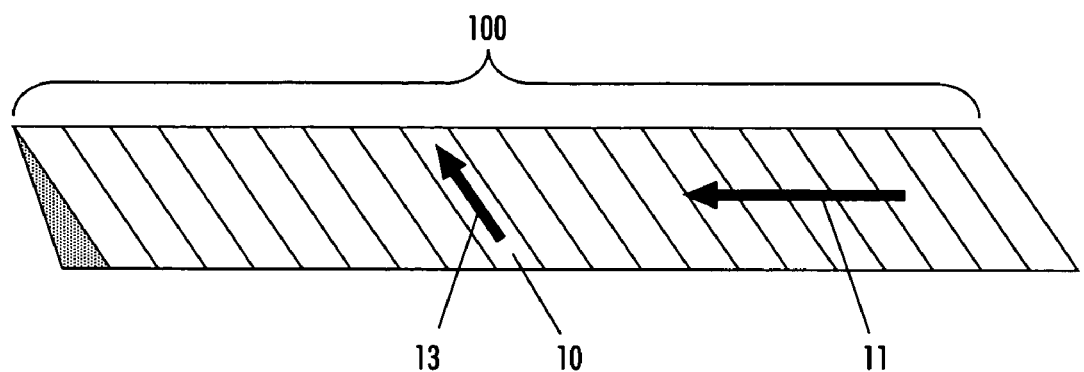
FIG. 1 is a schematic of a conventional wire form.

For a general understanding, reference is made to the drawings. In the drawings, like references have been used throughout to designate identical or equivalent elements. It is also noted that the drawings may not have been drawn to scale and that certain regions may have been purposely drawn disproportionately so that the features and concepts could be properly illustrated.

FIG. 1 illustrates a conventional wire form. As illustrated in FIG. 1, a lead 100 is constructed of a coiled conductor 10. The coiled conductor 10 may be a spring wire form. Conventionally, adjacent coils of the coiled conductor 10 are in contact with each other. The adjacent coils of the coiled conductor 10 are in electrical contact with each other, as noted above. The AC electric current mainly flows along the lead 100, as illustrated by arrow 11. Even when there is some electrical insulation between adjacent coiled loops, due to the parasitic capacitance and the AC induced current, a large portion of the current flows along the lead 100, as illustrated by arrow 11, and little current flows around the lead's loops, as illustrated by arrow 13. Thus the lead's electrical characteristic is mainly capacitive rather than inductive.

It is noted that the following descriptions of the various embodiments of the present invention, as well as the attached claims may utilize, the term wire form or lead, the term wire form or lead may generically refer to a unipolar pacing lead having one conductor; a bipolar pacing lead having two conductors; an implantable cardiac defibrillator lead; a deep brain stimulating lead having multiple conductors; a nerve stimulating lead; and/or any other medical lead used to deliver an electrical signal to or from a tissue area of a body.

In cases where there is not a significant electrical insulator between adjacent coiled loops, the current may flow from one loop to the next, along the length of the coil wire, through the adjacent loop contact points. In other cases where there is some electrical insulation between adjacent loops, more current flows around the loops. However, in situations where the current is an AC current of sufficient frequency, a significant portion of the current may still flow from one loop to the next without following around the loops due to parasitic capacitance between adjacent loops.

If the conventional lead 100 of FIG. 1 is subjected to a magnetic resonance imaging environment generating excitation signal of approximately 63.85 MHz, the conventional lead 100 of FIG. 1 would support significant AC currents (voltages) to cause a significant rise in the temperature over time to the area surrounding the conventional lead 100 of FIG. 1, thereby causing possible tissue damage. An example of this temperature rise is illustrated by trace A of FIG. 3.

Figure 2:
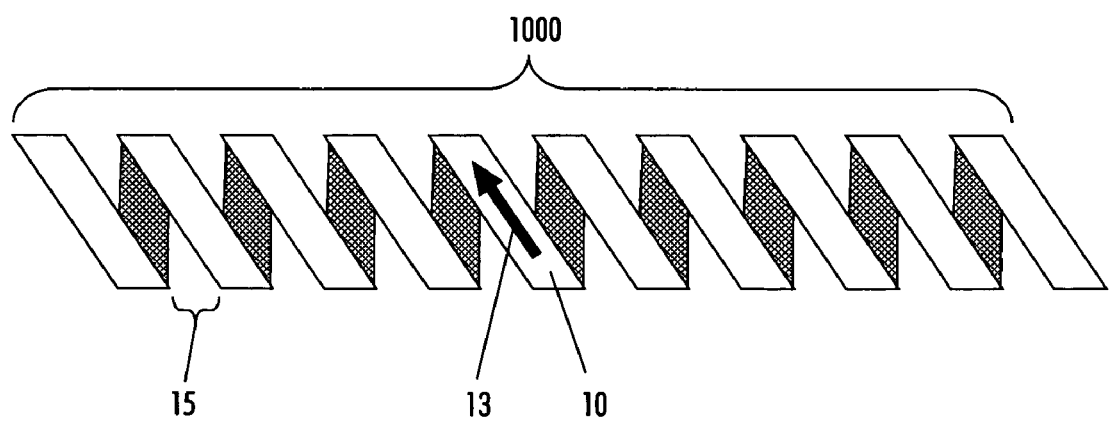
FIG. 2 is a schematic of a wire form according to the concepts of the present invention.

One reason for this possible significant temperature rise, as noted above, is that the conventional lead 100 of FIG. 1 has capacitive characteristics when exposed to the excitation signals of a magnetic resonance imaging environment, thus providing little impedance to current flow into and out of the lead. To reduce the temperature rise, the electrical characteristic of the lead when exposed to the excitation signals of a magnetic resonance imaging environment needs to reduce its parasitic capacitive characteristic and toward an increased inductive characteristic. FIG. 2 illustrates an example of a conventional wire form that has been modified so as to shift away from its adjacent loop parasitic capacitive characteristic and toward an inductive characteristic. In other words, the self-resonance of the wire form shifts towards the resonance frequency of the excitation signal of the magnetic resonance imaging scanner, thereby increasing the inductance and impedance characteristic of the wire form. In a preferred embodiment, the self-resonance of the wire form is approximately equal to the resonance frequency of the excitation signal of the magnetic resonance imaging scanner.

As Illustrated in FIG. 2, a lead 1000 is constructed of a coiled conductor 10. The coiled conductor 10 may be a spring wire form. Adjacent coils of the coiled conductor 10, unlike the conventional lead, are not in contact with each other. The adjacent coils of the coiled conductor 10 are spaced by a predetermined gap 15. Unlike the conventional lead, the flow of electric current follows the coiled conductor 10, as illustrated by arrow 13, thus increasing the lead's impedance.

The predetermined gap 15 changes the parasitic capacitance of the conventional lead and its inductance. More specifically, the modified lead's parasitic capacitance is lowered and the inductance is increased. In other words, the self-resonance of the wire form shifts towards the resonance frequency of the excitation signal of the magnetic resonance imaging scanner, thereby increasing the impedance characteristic of the wire form. In a preferred embodiment, the self-resonance of the wire form is approximately equal to the resonance frequency of the excitation signal of the magnetic resonance imaging scanner. Additionally, the lead may be adjusted such that it has a resonance frequency not tuned to an excitation signal's frequency of a magnetic-resonance imaging scanner.

If the lead 1000 of FIG. 2 is subjected to a magnetic resonance imaging environment generating excitation signals of approximately 63.85 MHz, the lead 1000 of FIG. 2 would support induced currents (voltages) to cause a less significant rise in the temperature over time to the area surrounding the conventional lead 1000 of FIG. 2, thereby reducing or eliminating the possibility of tissue damage. An example of this temperature rise is illustrated by trace B of FIG. 3.

To realize this modified lead, a conventional coiled lead may be stretched so as to form the predetermined gaps. The following table provides characteristics demonstrating how the stretching of a conventional lead can achieve the shifting of the characteristics.

TABLE

| WIRE | Resistance (Ohms) | Measured Characteristic @300 kHz | Resonance Freq. (MHz) | Measured Characteristic @approximately 63.85 MHz |
|---|---|---|---|---|
| Uncoated (26 cm) | 142.6 | 28.0 μH | 13.65 | 9.8 pF |
| Coated (26 cm) | 138.3 | 25.3 μH | 15.87 | 9.7 pF |
| Stretched Coated (45.7 cm) | | 24.0 μH | 18.40 | 10.2 pF |
| Stretched Coated (89 cm) | | 24.0 μH | 18.90 | 12.1 pF |

The Table shows that the uncoated wire does not have significantly less DC resistance than the coated wire, and at a magnetic resonance imaging scanner's approximately 63.85 MHz frequency, both uncoated and coated wire forms appear to behave as capacitors, not inductors.

As shown in the table, for a 26 cm long coiled wire form, the wire (self-resonance being 13.6 MHz) acts as a capacitor at approximately 63.85 MHz, having a capacitance of 9.8 pF and no measurable inductance.

As noted above, to reduce AC current flow at approximately 63.85 MHz what is needed is an increase in the wire forms inductance. This can be achieved by shifting the self-resonance of the wire form to some higher frequency.

In other words, the inductance of the wire form needs to increase, thereby shifting the self-resonance of the wire form toward the resonance frequency of the excitation signal of the magnetic resonance imaging scanner. In a preferred embodiment, the self-resonance of the wire form is approximately equal to the resonance frequency of the excitation signal of the magnetic resonance imaging scanner.

Figure 3:
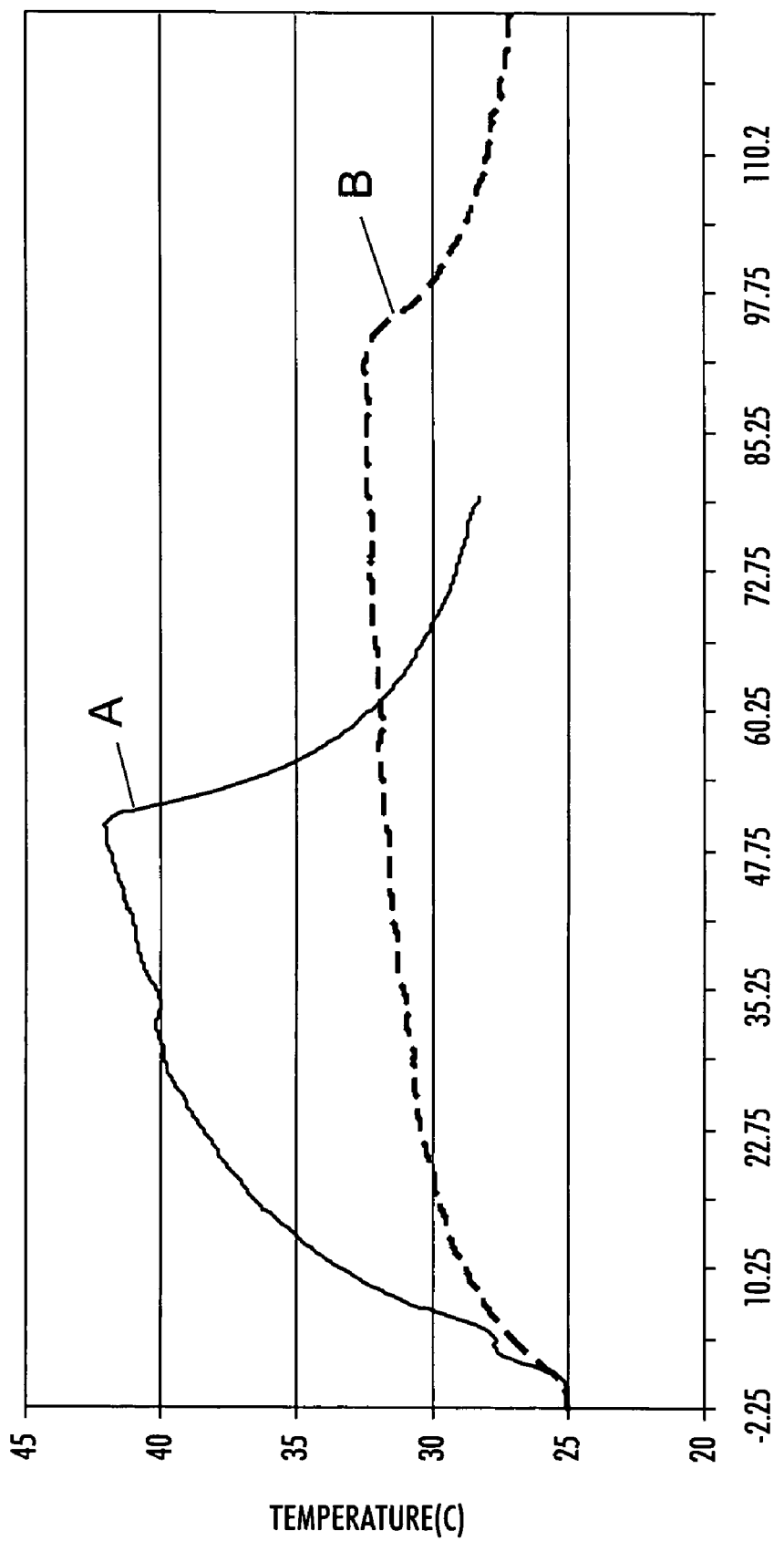
FIG. 3 is a graph showing a temperature generated by one embodiment of the present invention and a temperature generated by a conventional wire form.
Figure 4:
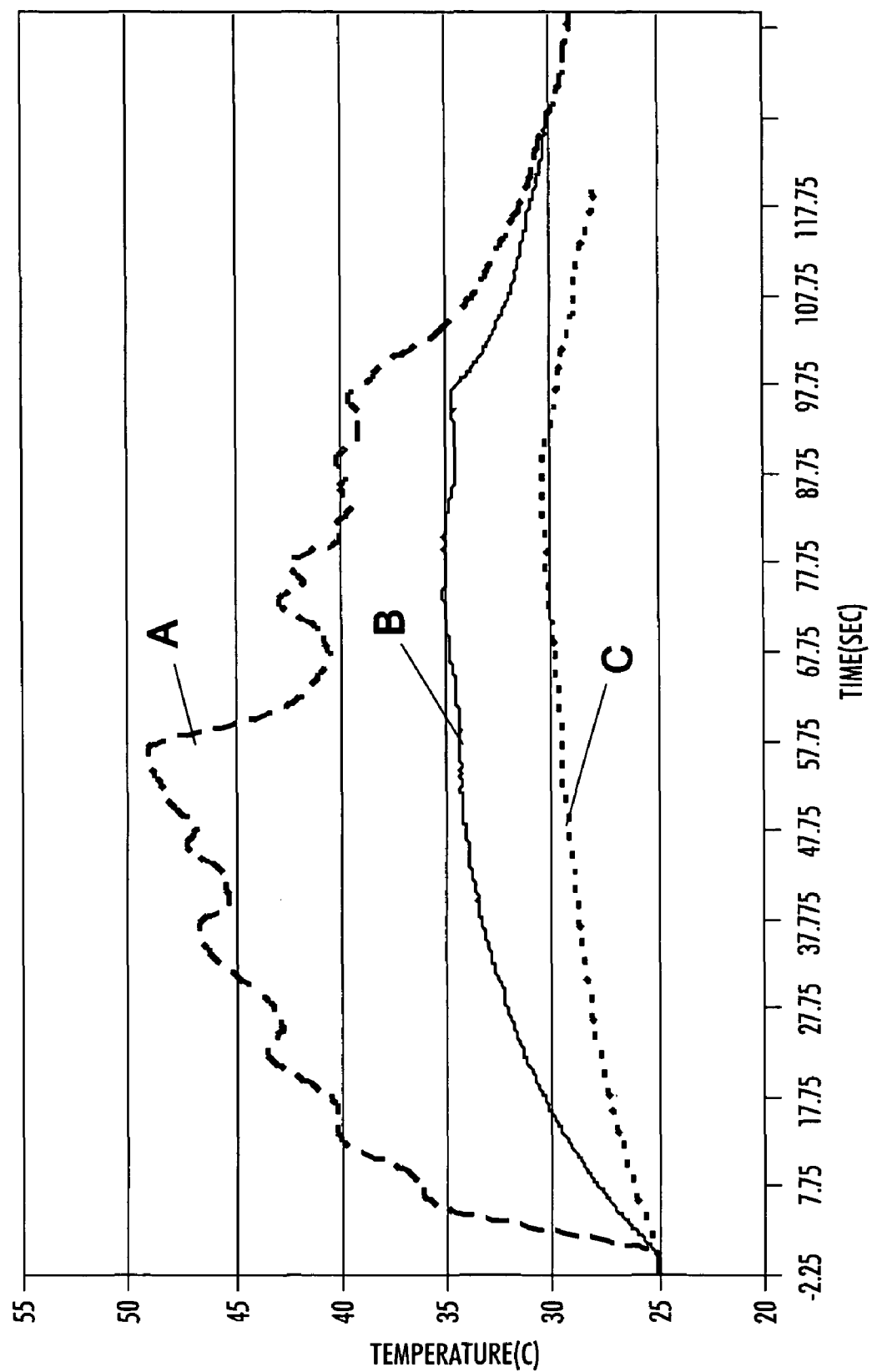
FIG. 4 is a graph showing a temperature generated by other embodiments of the present invention and a temperature generated by a conventional wire form.

This shifting can be realized by stretching apart the wire form. The stretching of the wire form causes the parasitic capacitance to change and the inductance to change. As illustrated in FIGS. 3 and 4, stretching the wire to an open form, space between each loop, the heating observed in a magnetic resonance imaging scanner can be reduced.

FIG. 3 is a temperature plot from experiments of two wire forms, both 26 cm wire forms, being subjected to a magnetic resonance imaging environment generating excitation signal of approximately 63.85 MHz. One wire is constructed, as illustrated in FIG. 1, with adjacent touching coiled loops. The other wire is stretched as illustrated in FIG. 2 with its adjacent coiled loops spaced apart, but still having an overall length of 26 cm. As illustrated in FIG. 3, the subjecting of an unstretched wire form to a magnetic resonance imaging environment generating excitation signal of approximately 63.85 MHz resulted in a significant rise in the temperature over time, illustrated by trace A of FIG. 3. On the other hand, the subjecting of a stretched wire form to a magnetic resonance imaging environment generating excitation signal of approximately 63.85 MHz resulted in a less significant rise in the temperature over time, thereby reducing or eliminating the possibility of tissue damage, illustrated by trace B of FIG. 3.

FIG. 4 is a temperature plot from three wire forms, all 52 cm wire forms, being subjected to a magnetic resonance imaging environment generating excitation signal of approximately 63.85 MHz. As illustrated in FIG. 4, the subjecting of an unstretched wire form to a magnetic resonance imaging environment generating excitation signal of approximately 63.85 MHz resulted in a significant rise in the temperature over time, illustrated by trace A of FIG. 4. Moreover, as illustrated in FIG. 4, the subjecting of an unstretched wire form, having an inductor in series therewith, to a magnetic resonance imaging environment generating excitation signal of approximately 63.85 MHz resulted in a significant rise in the temperature over time, illustrated by trace B of FIG. 4. On the other hand, the subjecting of a stretched wire form, having an inductor in series therewith, to a magnetic resonance imaging environment generating excitation signal of approximately 63.85 MHz resulted in a further reduction in the rise in the temperature over time, thereby reducing or eliminating the possibility of tissue damage, illustrated by trace C of FIG. 4.

Another option to stretching the wire form is to coat the wires before the wires are formed into a spring wire form. The wires are coated in 3 layers, an electrically insulative layer, an electrically conductive shielding layer, and a protective and electrically insulative layer. The coatings form a coaxial type wire. When the shielding layer is connected to ground, the parasitic capacitance is substantially eliminated and the coiled wire form has a larger inductance characteristic at approximately 63.85 MHz.

In other words, the self-resonance of the wire form shifts towards the resonance frequency of the excitation signal of the magnetic resonance imaging scanner, thereby increasing the inductance characteristic of the wire form. In a preferred embodiment, the self-resonance of the wire form is approximately equal to the resonance frequency of the excitation signal of the magnetic resonance imaging scanner.

A further option is to use existing small coaxial wire to form the spring wire form.

As discussed above, the stretching of a spring wire form changes the AC characteristics of the wire form so as to shift the characteristics of the wire form from being capacitive to being inductive. This inductance has the ability to significantly reduce current flow through the lead due to multiple causes.

Moreover, the use of coating or a coaxial cable can also change the AC characteristics of the wire form so as to shift the characteristics of the wire form from being capacitive to being inductive, thereby significantly reducing current flow through the lead due to multiple causes.

While various examples and embodiments of the present invention have been shown and described, it will be appreciated by those skilled in the art that the spirit and scope of the present invention are not limited to the specific description and drawings herein, but extend to various modifications and changes.

What is claimed is:

1. An implantable medical lead having a length that extends from a proximal end configured to be coupled to a medical device to a distal end configured to be implanted in a heart of a patient, the lead comprising:
    an electrode located near the distal end of the lead; and
    a conductor in the lead having a distal end proximate the electrode and a proximal end proximate the medical device;
    said conductor being coiled; said conductor having a predetermined spacing between adjacent coils extending along a length of the conductor from the distal end of the conductor to the proximal end of the conductor, said predetermined spacing providing a parasitic capacitance and an inductance, said parasitic capacitance and inductance having a resonance frequency approximately equal to an excitation signal's frequency of a magnetic resonance imaging scanner.

2. The lead as claimed in claim 1, wherein said conductor is a spring wire form coated with an electrically insulative layer, an electrically conductive shielding layer, and a protective and electrically insulative layer.

3. The lead as claimed in claim 1, wherein said conductor is a first conductor in a bipolar pacing lead and said electrode is a first electrode, the lead further comprising:
    a second electrode located near the distal end of the lead; and
    a second conductor in the lead having a distal end proximate the second electrode and a proximal end proximate the the medical device;
    said second conductor being coiled; said second conductor having a predetermined spacing between adjacent coils extending along a length of the conductor from the distal end of the conductor to the proximal end of the conductor, said predetermined spacing providing a parasitic capacitance and an inductance, said parasitic capacitance and inductance having a resonance frequency approximately equal to an excitation signal's frequency of the magnetic resonance imaging scanner.

4. The lead as claimed in claim 1, wherein said conductor is a conductor in a unipolar pacing lead.

5. The lead as claimed in claim 1, wherein said conductor is a conductor in a cardiac defibrillator lead.

6. The lead as claimed in claim 1, wherein the conductor in the lead is adapted to conduct electrical stimulating pulses from the circuitry of the medical device to sites within a heart via the electrode and conduct sensed signals from the electrode to the circuitry of the medical device.

7. A system comprising:
    an implantable medical device including:
        a case that includes circuitry housed within the case; and
        a connector block mounted on the case, wherein the connector block includes at least one receptacle for a lead and an electrical interface to electrically connect the lead with the circuitry of the implantable medical device; and
    an implantable medical lead including:
        a proximal end coupled to the receptacle;
        a distal end;
        an electrode located near the distal end; and
        a coiled conductor in the lead having a distal end proximate the electrode and a proximal end proximate the electrical interface to provide an electrical circuit path from the electrode to the circuitry of the implantable medical device;
        wherein adjacent coils of the coiled conductor have a predetermined spacing to provide a parasitic capacitance and an inductance having a resonance frequency approximately equal to an excitation signal's frequency of a magnetic resonance imaging scanner.

8. The system as claimed in claim 7, wherein said conductor is a spring wire form coated with an electrically insulative layer, an electrically conductive shielding layer, and a protective and electrically insulative layer.

9. The system as claimed in claim 7, wherein said conductor is a first conductor in a bipolar pacing lead and said electrode is a first electrode, the lead further comprising:
    a second electrode; and
    a second coiled conductor in the lead having a distal end proximate the second electrode and a proximal end proximate the electrical interface to provide an electrical circuit path to the circuitry of the implantable medical device;
    wherein adjacent coils of the second coiled conductor have a predetermined spacing to provide a parasitic capacitance and an inductance having a resonance frequency approximately equal to an excitation signal's frequency of a magnetic resonance imaging scanner.

10. The system as claimed in claim 7, wherein said conductor is a conductor in one of a unipolar pacing lead and a cardiac defibrillator lead.

11. The system as claimed in claim 7, wherein the conductor in the lead is adapted to conduct electrical stimulating pulses from the circuitry of the medical device to sites within a heart via the electrode and conduct sensed signals from the electrode to the circuitry of the medical device.

12. The system as claimed in claim 7, wherein the coiled conductor contacts the electrode at the distal end and contacts the electrical interface at the proximal end to provide the electrical circuit path.

13. An implantable medical lead having a length that extends from a proximal end configured to be coupled to a medical device to a distal end configured to be implanted in a heart of a patient, the lead comprising:
  an electrode located near the distal end of the lead; and
  a coiled conductor that extends substantially the length of the lead such that a proximal end of the conductor is located proximate the medical device and a distal end of the conductor is located proximate the electrode;
  wherein adjacent coils of the coiled conductor have a predetermined spacing to provide a parasitic capacitance and an inductance having a resonance frequency approximately equal to an excitation signal's frequency of a magnetic resonance imaging scanner.

14. The implantable medical lead of claim 13, wherein the adjacent coils of the coiled conductor extend from the proximal end of the conductor to the distal end of the conductor.

* * * * *